United States Patent [19]
Halloran et al.

[11] Patent Number: 5,733,537
[45] Date of Patent: *Mar. 31, 1998

[54] HAIR FIXATIVES

[75] Inventors: Daniel Joseph Halloran; Judith Merrane Vincent, both of Midland, Mich.

[73] Assignee: Dow Corning Corporation, Midland, Mich.

[*] Notice: The term of this patent shall not extend beyond the expiration date of Pat. No. 5,075,103.

[21] Appl. No.: 729,281

[22] Filed: Jul. 12, 1991

Related U.S. Application Data

[63] Continuation of Ser. No. 548,810, Jul. 6, 1990, Pat. No. 5,075,103.

[51] Int. Cl.$^6$ ........................................ A61K 7/11
[52] U.S. Cl. ........................... 424/70.121; 424/47
[58] Field of Search ........................ 424/47, 71, 78, 424/DIG. 1, DIG. 2

[56] References Cited

U.S. PATENT DOCUMENTS

| | | | |
|---|---|---|---|
| 2,676,182 | 4/1954 | Daudt et al. | 524/860 |
| 2,891,920 | 6/1959 | Hyde et al. | 524/714 |
| 3,378,575 | 4/1968 | Brown et al. | 556/459 |
| 3,964,500 | 6/1976 | Drakuff | 424/70 |
| 4,175,159 | 11/1979 | Raliegh | 428/447 |
| 4,424,297 | 1/1984 | Bey | 524/714 |
| 4,983,383 | 1/1991 | Maksimoski et al. | 424/71 |
| 5,049,377 | 9/1991 | Lamb et al. | 424/71 |
| 5,075,103 | 12/1991 | Halloran et al. | 424/71 |
| 5,126,126 | 6/1992 | Varapath et al. | 424/71 |
| 5,135,742 | 8/1992 | Halloran et al. | 424/71 |
| 5,152,984 | 10/1992 | Varapath et al. | 424/71 |
| 5,173,290 | 12/1992 | Halloran | 424/71 |
| 5,180,580 | 1/1993 | Halloran et al. | 424/71 |
| 5,194,251 | 3/1993 | Halloran et al. | 424/71 |
| 5,194,260 | 3/1993 | Grollier et al. | 424/71 |

FOREIGN PATENT DOCUMENTS

| | | |
|---|---|---|
| 240350 | 10/1987 | European Pat. Off. . |
| 333433 | 9/1989 | European Pat. Off. . |

OTHER PUBLICATIONS

Encyclopedia of Polymer Science & Technology, vol. 12, 1970, John Wiley & Sons, Inc. p. 500.
Cosmetic Aerosol Products, Johnsen Cosmetics & Toiletries pp. 27–32, vol. 97, Jan. 1982.

*Primary Examiner*—Amy Hulina
*Attorney, Agent, or Firm*—Sharon K. Severance

[57] ABSTRACT

A hair treating method for imparting curl retention to hair in which at least one film forming ingredient is applied to the hair. The improvement utilizes as the film forming ingredient an organosilicon compound which is a nonpolar silsesquioxane. Hair fixative compositions including the nonpolar silsesquioxane are also disclosed.

9 Claims, No Drawings

HAIR FIXATIVES

This is a continuation of application Ser. No. 07/548,810 filed on Jul. 6, 1990, now U.S. Pat. No. 5,075,103.

BACKGROUND OF THE INVENTION

This invention relates to new hair fixative compositions and to improved methods of providing curl retention to hair in which there is employed as the film forming ingredient certain organosilicon resins which are nonpolar silsesquioxanes.

Fixatives are designed to provide a temporary setting effect or curl to the hair, and while the most common fixative is a hair spray which is designed to be applied to the hair after the hair has been blow dried, several specialty type fixatives can be applied either after the hair is towel dried or to dry hair, in order to provide more body and volume to the hair, and to aid in styling, modeling, and sculpting of the hair into unique new looks. This is followed by application of a hair spray in the form of an aerosol or pump spray to maintain the shape and style of the hair and provide gloss and sheen to the hair, in addition to a well groomed and natural appearance. Such specialty type fixatives are marketed under various names including styling gels, styling cremes, styling mousses, styling foams, styling sprays, styling spritz, styling mists, styling glazes, styling fixes; sculpting lotions, sculpting Eels, sculpting glazes, sculpting sprays; glossing Eels, glossing spritz; shaping gels; forming mousses; modeling spritz; finishing spritz; fixing gels; and setting lotions.

Whether the fixative is the more common hair spray or a specialty type fixative, it will typically include a film forming additive as the hair holding agent. The film forming additive should provide hair holding properties and curl retention, little flaking or powder on combing, rapid curing or drying on hair, nonstickiness, and be easily removable by shampooing. Film forming additives are delivered by a solvent which is usually an alcohol such as ethanol or a mixture of an alcohol and water. In the case of aerosol formulations such as hairsprays and mousses, a propellant such as isobutane, butane, propane or dimethyl ether is an added part of the delivery system.

Examples of currently used film forming agents are shellac, polyvinylpyrrolidone-ethyl methacrylate-methacrylic acid tarpolymer, vinyl acetate-crotonic acid copolymer, vinyl acetate-crotonic acid-vinyl neodeconate tarpolymer, poly(vinylpyrrolidone-ethylmethacrylate) methacrylic acid copolymer, vinyl methyl ether-maleic anhydride copolymer, octylacrylamide-acrylate-butylaminoethyl-methacrylate copolymer, and poly(vinylpyrrolidone-dimethylaminoethyl-methacrylate) copolymer and derivatives. These particular polymers are most suitable for alcohol based formulations such as hair sprays and pumps, and are sometimes used in water-based hair fixative products.

Such resins typically contain carboxyl groups which must be neutralized to some degree to provide compatibility with water to facilitate removal by shampooing and to increase the flexibility of the film. The neutralization of the carboxyl groups can lead to relatively high solution viscosities. Furthermore, the high molecular weight of the better holding resins produces solutions which are high in viscosity. When loading is attempted above a level of six to seven percent by weight of the formulation, the high viscosity prevents the solution from breaking up into droplets, and a stream rather than a spray is produced. Although higher solids solutions of these resins are deliverable from containers which have a small orifice, these valves are more prone to clogging. Thus, loading of these resins above a certain solids level is not practical. In addition these organic resins have poor hold when subjected to high humidity for long periods of time.

Thus, a need exists for a fixative resin which is water compatible without neutralization, provides high humidity resistance, is compatible with hydrocarbon propellants and is capable of being formulated into high solids products.

In accordance with the present invention, a new hair fixative formulation is provided which includes an organosilicon film forming material. Specifically, the organosilicon film forming material is a silicone resin, and more particularly a nonpolar silsesquioxane. Silsesquioxanes are not new. For example, collodial suspensions of silsesquioxanes are disclosed in U.S. Pat. No. 3,433,780, issued Mar. 18, 1969; U.S. Pat. No. 3,493,424, issued Feb. 3, 1970; and in U.S. Pat. No. 4,424,297, issued Jan. 3, 1984. However, these patents relate to the use of silsesquioxanes for the treatment of fabrics to render them resistant to soiling and as fillers in latexes; the treatment of fabric or carpeting in order to impart antislip, dulling, and dry-soiling resistance to the materials; and as release agents. Thus, there is no suggestion in these patents that a silsesquioxane would have utility as a film forming ingredient in a hair fixative formulation. While U.S. Pat. No. 4,902,499, issued Feb. 20, 1990, relates to the use of silicone resins in hair care compositions, the '499 patent does not teach the particular silicone resins of the present invention which are nonpolar silsesquioxanes.

The '499 patent is also specifically directed to compositions which provide improved style retention and hair conditioning properties. To that end, conditioning moleties such as dialkylsiloxane are prominent. It is known that conditioning can adversely affect holding properties in fixative formulations. Therefore, the dialkylsiloxane moieties are eliminated or reduced in the present invention. Thus, this invention employs silsesquioxane resins for set retention with improved hair-holding properties.

Silicones have two inherent properties particularly advantageous in hair holding applications. Certain silicone materials form films which are hydrophobic and produce solutions of low viscosity. The nonpolar silsesquioxanes of the present invention have been found to provide higher humidity resistance than organic film forming materials at lower add-on levels. In contract to the organic resins, their solution viscosity is low, even at high loading. This characteristic provides resins which can be formulated at higher solids levels than permitted by current formulations.

An unexpected benefit derived from low solution viscosity is the improved spray patterns that the materials of the present invention exhibit when delivered through an orifice of industry standard size. Even at solids levels as high as 15 percent by weight, the silsesquioxane solutions yield well-dispersed spray patterns. Unlike the organic film formers, the silsesquioxanes do not require neutralization to provide water compatibility. Additionally, the materials of the present invention permit variations in hold from harsh to soft hold through structure modifications. This is in contrast again to the organic polymers which are harsh holding when minimally neutralized and can only provide soft hold through neutralization, which in turn, compromises high humidity resistance. Furthermore, the silsesquioxanes offer additional advantages including compatibility with ethanol and hydrocarbon propellants, good sheen, low buildup, nontacky, nonirritability, and reduced flaking.

SUMMARY OF THE INVENTION

This invention is directed to a hair treating method for imparting curl retention to hair in which at least one film forming ingredient is applied to the hair. The improvement utilizes as the film forming ingredient an organosilicon compound. The organosilicon compound is a silicone resin which is a nonpolar silsesquioxane.

This invention is also directed to a hair treating method for imparting curl retention to hair in which a film is formed on the hair, and the film is an organosilicon compound which is a nonpolar silsesquioxane.

The invention is further directed to hair fixative compositions for imparting curl retention to hair which include an organosilicon compound which is a silicone resin and a nonpolar silsesquioxane.

These and other features, objects, and advantages, of the present invention will become more apparent when considered in light of the following detailed description thereof.

DETAILED DESCRIPTION OF THE INVENTION

As noted above, the present invention relates to hair fixatives which utilize as the film forming ingredient a silicone resin which is a nonpolar silsesquioxane. Such silicone resins have been found to exhibit improved curl retention in comparison to conventional organic systems, and provide the advantages of ethanol solubility, water compatibility, nonirritability, excellent aesthetics on hair, excellent shampoo removability, good sheen, improved hold, low buildup, nontacky, and reduced flaking. The silicone resins of the present invention also offer the added benefit that a plasticizer is not required, although plasticizers may be included in the fixative composition if desired. Typical organic fixative systems include what are known in the trade as GANTREZ® resins which are polymers consisting of the partial ethyl ether of the polycarboxylic resin formed from vinyl methyl ester and maleic anhydride. One of the more popular GANTREZ® resins is GANTREZ® ES 225, a product of the GAF Corporation, Wayne N.J. GANTREZ® is also a trademark of the GAF Corporation. This resin has been the film forming ingredient in such products as WHITE RAIN® and FINAL NET®. Such resins are typically employed as an ethanol based pump spray.

Several commercial hair fixative formulations are water based and include deep conditioners, styling gels, and mousses. While not primarily a hair fixative, the deep conditioners may contain a water soluble resin for imparting some degree of set retention. The most popular organic film forming ingredient in such water based organic systems is known in the trade as the GAFQUAT® resins. Such resins are also products of the GAF Corporation, Wayne, N.J., and GAFQUAT® is a trademark of that company. Exemplary of the commercial resins are GAFQUAT® 734 and GAFQUAT® 755, otherwise known under the designation Polyquaternium-11, an adopted name of the Cosmetic, Toiletry, and Fragrance Association. While organosilicon compounds are not known to be water soluble, the silicone resin materials of the present invention are soluble or compatible in water based systems and hence possess utility in such systems in place of the organic GAFQUAT® variety of resin currently employed in the art.

The nonpolar silsesquioxanes also have application in aqueous-alcohol based hair fixative systems. Aqueous ethanol, for example, is employed in some commercial spray-on pump and aerosol type products and mousses. The function of the alcohol in such systems is to promote faster drying of the formulation relative to the water based type system. In addition, the nonpolar silsesquioxanes of the present invention may be used in anhydrous alcohol systems whether the system is designed for aerosol delivery or delivery by means of a pump spray device.

In the hair treating method in accordance with the present invention, the film forming ingredient is an organosilicon compound which is a nonpolar silsesquioxane having a formula selected from the group consisting of

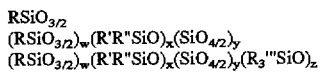

and hydroxy, alkoxy, aryloxy, and alkenoxy, derivatives thereof, wherein R, R', R", and R''', are selected from the group consisting of alkyl, alkenyl, aryl, and alkylaryl, radicals having from one to twenty carbon atoms; and w, x, y, and z, are each integers having a value of from zero to about one thousand, with the proviso that the sum of integers w and y must be at least one.

The nonpolar silsesquioxane silicone resin materials conforming to any one of the above specified generic formulas are commercially available from the Dow Corning Corporation, Midland, Mich.

These nonpolar silsesquioxanes are applied to the hair as a mixture including a solvent. The organosilicon compound is present in the mixture at a level from about 0.1 to about fifty percent by weight based on the weight of the mixture. Preferably, the organosilicon compound is present in the mixture at a level from about three to about thirty percent by weight based on the weight of the mixture. The solvent may be water, a hydrocarbon, an alcohol, or a blend of alcohol and water. Other solvents which may be employed include supercritical fluids such as supercritical carbon dioxide and nitrogen; volatile silicones including linear and cyclic siloxanes; non-volatile hydrocarbons; and in some instances aqueous emulsion systems may also be appropriate. Where the solvent is a hydrocarbon, it is preferred to employ materials such as dimethylether, liquefied petroleum gas, propane, and isobutane. In the event the solvent is an alcohol, some appropriate materials are methanol, ethanol, and isopropanol.

One example of a compound in accordance with the present invention is a silsesquioxane of the formula

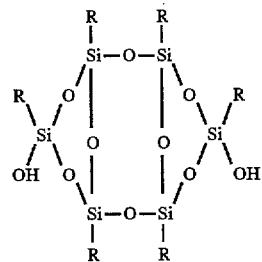

This material can be applied to the hair as a mixture including a solvent, and in addition, if desired, at least one additional ingredient such as propellants, conditioners, surfactants, plasticizers, thickeners, preservatives, and fragrances.

The nonpolar silsesquioxanes of the present invention were dissolved in ethanol and tested for curl retention. These formulations were compared to a commercial aerosol product containing GANTREZ® as the film forming resin ingredient. The resin materials of the present invention provided curl retentions beyond the curl retention obtained with the commercial product. In experiments involving multiple hair tresses, the materials of the present invention provided more consistent results than the corresponding commercial product. The results of these tests and their procedures are set forth below.

The following examples are set forth in order to illustrate in more detail the concepts embodied by the present invention.

EXAMPLE I

Into a three neck round bottom flask equipped with a stirrer and thermometer was placed 39.8 grams toluene and 14.4 grams isopropanol. To this was added 33.6 grams phenyltrichlorosilane and 12.2 grams propyltrichlorosilane. Water was added to hydrolyze the chlorosilanes in an amount to produce an aqueous phase containing 13–16 weight percent hydrochloric acid. This mixture was refluxed for four hours insuring continuous hydrolysis. The hydrolyzate was separated from the aqueous phase, the solvent was removed under vacuum, and the solid product was flaked. The product corresponded to a nonpolar silsesquioxane of the formula $RSiO_{3/2}$.

EXAMPLE II

The silsesquioxane of Example I was formulated into a hair fixative composition by mixing with ethanol in order to provide various fixative formulations containing 1.5, two, three, and five percent by weight of the silane hydrolyzate.

EXAMPLE III

Hair fixative formulations were evaluated by employing six inch hair tresses of approximately two grams of untreated human hair. Each tress was made by gluing the top part of the hair to a 2"×2" plastic tab. After drying on the tab, the hair was trimmed to six inches. Each tress was then cleaned with an anionic/amphoteric shampoo of the following formulation:

| | |
|---|---|
| Distilled Water | 61.45% |
| Methylchlorisothiazolinone and methylisothiazolinone | 0.05% |
| Ammonium Lauryl Sulfate | 35.00% |
| Lauramide DEA | 3.00% |
| Sulfuric Acid | q.s. |
| Ammonium Chloride | 0.50% |

The tress was first rinsed for 15 minutes under 40 degree Centigrade tap water and 0.5 cc of the above shampoo was applied. Shampooing for 30 seconds was followed by a 30 second rinse. The tresses were then set on plastic rollers approximately ½ in. in diameter and allowed to dry overnight. Hair fixative formulations were applied to the hair either by dripping on 0.5 g or by spraying on 0.3 g. If the drip application was used, the hair was combed three times and reset on a roller. If the resin solution was delivered from a pump, the hair was not reset. The solution was allowed to cure on the hair for a period of one to two hours. The dried tresses were hung in a constant humidity chamber at 90 percent relative humidity and initial readings were taken as well as additional readings at predetermined intervals. If the tress was reset, the roller was removed prior to exposure. Curl retention was calculated as the extended length minus the length at the end of the predetermined interval divided by the extended length minus the initial length. The results shown in Table I represents curl retention after 24 hours of exposure.

GANTREZ ES225 resin, which is a polymer of the partial ester of the carboxylic resin formed from vinyl methyl ester and maleic anhydride, was used as the control comparison. This organic resin is frequently used in ethanol based hair holding formulations such as aerosols and pumps.

TABLE I

| | Curl Retention (Percent) |
|---|---|
| Percent Silsesquioxane in Ethanol | |
| 1.5 | 84 |
| 2.0 | 84 |
| 3.0 | 92 |
| 5.0 | 96 |
| Percent Gantrez ® in Ethanol | |
| 1.5 | 0 |
| 2.0 | 0 |
| 3.0 | 73 |
| 5.0 | 93 |

EXAMPLE IV

Into a three neck round bottom flask equipped with a stirrer and thermometer was placed 42.3 grams toluene and 7.6 grams isopropanol. To this was added 22.7 grams phenyltrichlorosilane, 18.2 grams of methyltrichlorosilane, 2.5 grams of phenylmethyltrichlorosilane, and 6.8 grams of diphenyldichlorosilane. Water was added to hydrolyze the chlorosilanes in an amount to produce an aqueous phase containing 13–16 weight percent hydrochloric acid. This mixture was refluxed for four hours insuring continuous hydrolysis. The hydrolyzate was separated from the aqueous phase, the solvent was removed under vacuum and the solid product was flaked. The product corresponded to a nonpolar silsesquioxane of the formula $(RSiO_{3/2})_w(R'R''SiO)_x(SiO_{4/2})_y$.

EXAMPLE V

The silsesquioxane of Example IV was formulated into a hair fixative composition by mixing with ethanol in order to provide various fixative formulations containing two, three, and five percent by weight of the silane hydrolyzate.

EXAMPLE VI

The hair fixative formulations of Example V were evaluated according to the procedure described in Example III. The organic resin GANTREZ® ES225 was used as the control comparison. The results of these evaluations are given below.

TABLE II

| | Curl Retention (Percent) |
|---|---|
| Percent Silsesquioxane in Ethanol | |
| 2.0 | 86 |
| 3.0 | 92 |
| 5.0 | 94 |
| Percent Gantrez ® in Ethanol | |
| 2.0 | 0 |
| 3.0 | 73 |
| 5.0 | 93 |

Compounds preferred in accordance with the present invention are those compounds which are produced from the chlorosilanes or alkoxysilanes shown in Table III.

TABLE III

Mole Percent Ratios of Preferred Silane

| Resin | Me | Me2 | Ph | Ph2 | PhMe | Pr | Me3 | Weight Percent Metallic Salt |
|---|---|---|---|---|---|---|---|---|
| 1 | — | — | 70 | — | — | 30 | — | — |
| 2 | 45 | — | 40 | 10 | 5 | — | — | — |
| 3 | 32 | 29.3 | 38.7 | — | — | — | — | — |
| 4 | 63–66 | 0.8 | 31–33 | — | — | — | 0.7 | — |
| 5 | 60 | — | 30 | 10 | — | — | — | — |
| 6 | 25 | 19 | 37 | 19 | — | — | — | — |
| 7 | 25 | 19 | 37 | 19 | — | — | — | 1.2* |

*Zinc Octoate added at 1.2 percent based on weight of resin.

EXAMPLE VII

The process used to make the silsesquioxane of this example is set forth in U.S. Pat. No. 2,676,182. A general description follows. 22.0 grams sodium silicate was added to a refrigerated flask equipped with a stirrer and thermometer. To this was added 19.3 grams hydrochloric acid. After exotherm, 6.9 grams of isopropanol and 22.0 grams of trimethylchlorosilane was added, heat applied and refluxing continued for a period of time. 1.8 grams polydimethylsiloxane was added and heating was continued. The product was separated from the aqueous phase and the resulting material was the nonpolar silsesquioxane of the formula

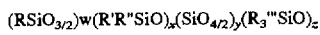

at a weight percent level of 46 and

at a weight percent level of 54.

EXAMPLE VIII

The silsesquioxane of Example VII was formulated into a hair fixative composition by mixing with $Me_3SiOSiMe_3$ in order to provide various fixative formulations containing five and ten percent by weight of the silsesquioxane. This Example illustrates the delivery of a silicone hair holding compound from a volatile silicone solvent.

EXAMPLE IX

The hair fixative formulations of Example VIII were evaluated according to the procedure described in Example III. An organic control was not employed due to limited solubility in volatile silicones. The results of these evaluations are set forth in Table IV.

TABLE IV

| Percent Silsesquioxane in Polydimethylsiloxane | Curl Retention (Percent) |
|---|---|
| 5.0 | 92 |
| 10.0 | 91 |

EXAMPLE X

The silsesquioxane of Example I was diluted in ethanol to a level of 10 percent by weight. Comparisons of this solution and the ten percent solution of Example VII were made to a 10 percent solution of GANTREZ ES225 in ethanol in terms of solution viscosity, spray pattern, curl retention and subjective aesthetic evaluation of hold. Kinematic viscosity was determined by use of a Cannon-Fenske Routine Viscometer, size 100, at 22° C. according to Standard Test ASTM D 445. Spray patterns were observed by spraying resin solutions through a CALMAR Mark II spray pump having a 0.012 inch sheet of solvent sensitive paper. In the case of Example VIII, which is solvent free, a dye was added to the resin solution to provide the spray pattern. Curl Retention was determined according to Example III and the solution was applied via the CALMAR Mark II Pump. Aesthetics refers to the feel of the set hair prior to humidity exposure. The results of these evaluations are set forth in Table V.

TABLE V

| Resin Solution | Viscosity (cs) | Spray Pattern | Curl Retention | Aesthetics |
|---|---|---|---|---|
| GANTREZ | 17.1 | stream | 94% | harsh hold |
| Example I | 2.3 | fine spray | 99% | harsh hold |
| Example VIII | 0.8 | fine spray | 94% | soft hold |

The compositions of this invention may contain an emulsifying agent selected from the group consisting of anionic, amphoteric, nonionic, cationic, and zwitterionic surfactants. Suitable anionic detergents include sulfonated and sulfated alkyl, aralkyl and alkaryl anionic detergents; alkyl succinates; alkyl sulfosuccinates and N-alkyl sarcosinates.

Surfactants generally classified as amphoteric or ampholytic detergents include, among others, cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine. Other suitable amphoteric detergents include the quaternary cycloimidates, betaines, and sultaines disclosed in U.S. Pat. No. 3,964,500.

The compositions of this invention may contain a nonionic surfactant. The nonionic surfactants of the present invention are selected from the group consisting of fatty acid alkanolamide and amine oxide surfactants.

Appropriate cationic surfactants in accordance with the present invention include quaternary ammonium salts of primary, secondary, and tertiary fatty amines. Zwitterionic surfactants which may be employed are quaternary ammonium, phosphonium, and sulfonium compounds containing aliphatic substituents one of which is carboxy, phosphate, phosphonate, sulfate, or sulfonate functional.

Other adjuvants may be added to the compositions of this invention such as plasticizers, thickeners, perfumes, colorants, electrolytes, pH control ingredients, antimicrobials, antioxidants, ultraviolet light absorbers and medicaments. When the fixative is in the form of a gel or lotion, it is sometimes preferred to employ a thickener in the compositions to facilitate the hand application of the composition to the hair. Thickeners are preferably used in sufficient quantities to provide a convenient viscosity. For example, viscosities within the range of 400 to 6000 cps are preferred for lotions. Higher viscosities are preferred for gels whereas lower viscosities are preferred for sprays.

Suitable thickeners, include, among others, sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose, and starch amylose, locust bean gum, electrolytes such as NaCl, saccharides such as fructose and glucose, and derivatives of saccharides such as PEG-120 methyl glucose dioleate. Preferred thickeners include the cellulose derivatives and saccharide derivatives. The glucose derivative, PEG-120 methyl glucose dioleate, is especially preferred in the present invention. Electrolytes including sodium chloride and ammonium chloride provide thickening particularly in aqueous systems and may also be employed in accordance with the present invention.

Representative plasticizers that may be employed include polyproplylene glycol, glycerine, and polysiloxanes. Siloxane polymers such as polydimethylsiloxane, cyclic polydimethylsiloxane, phenylpolydimethylsiloxane, and polydimethylsiloxane with methylene and or propylene oxide side chains, are particularly preferred in accordance with the present invention.

The perfumes which can be used in the compositions are the cosmetically acceptable perfumes. Colorants are used to confer a color to the composition and may generally be used. Although not required, it is preferred to employ an acid or base to adjust the pH within the range of 5 to 9 or more preferably within the range of 6 to 8 in the compositions of this invention. Any water soluble acid such as a carboxylic acid or a mineral acid is suitable. For example, suitable acids include mineral acids such as hydrochloric, sulfuric, and phosphoric, monocarboxylic acids such as acetic acid, lactic acid, or propionic acid; and polycarboxylic acids such as succinic acid, adipic acid and citric acid. Where a base is required, organic amines such as 2-amino-2methyl-1-propanol are appropriate.

If for special purposes conditioners are desired, they may be added. For example, any of the well-known organic cationic hair conditioning components may be added. Some cationic conditioning components that may be used in the present invention to provide hair grooming include quaternary nitrogen derivatives of cellulose ethers, homopolymers of dimethyldiallyl-ammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-α,ω-bis-(triethanolammonium) chloride, and copolymers of vinylpyrrolidone and acrylic acid esters with quaternary nitrogen functionality. The above cationic organic polymers and others are described in more detail in U.S. Pat. No. 4,240,450 which is hereby incorporated by reference to further describe the cationic organic polymers. Other categories of organic conditioners may also be employed such as proteins, monomeric organic quaternarys and betaines. Silicone conditioning agents may also be employed such as cyclomethicone, dimethicone, phenyldimethicone, dimethicone copolyol, amodimethicone, and trimethylsilylamodimethicone.

A preservative may be required and representative preservatives which may be employed include about 0.1–0.2 weight percent of compounds such as formaldehyde, dimethyloldimethylhydantoin, 5-bromo-5-nitro-1,3-dioxane, methyl- and propyl para-hydroxybenzoates, and mixtures of such benzoates with sodium dehydroacetate, sorbic acid, and imidazolidinyl urea.

The compositions of the present invention may also be formulated to include dyes, colorants, reducing agents, neutralizing agents, and preservatives, necessary for their application as permanent wave systems or hair dyes, for example. The active formulation can be applied in several different forms including lotions, gels, mousses, aerosols, and pump sprays, for example, and as conditioners and shampoos. The active ingredient includes a carrier, and suitable carrier fluids for hair care formulations are water as well as, for example, such fluids as alcohols namely ethanol or isopropanol, hydrocarbons and halogenated hydrocarbons such as mineral spirits and trichloroethane, supercritical fluids such as supercritical carbon dioxide and nitrogen, cyclic siloxanes, and aerosol propellants. In those instances where it is desired to incorporate the active in the form of either an emulsion or microemulsion, such emulsions may be prepared in accordance with either U.S. Pat. No. 4,501,619, issued Feb. 26, 1985, which is directed to emulsions, or U.S. Pat. No. 4,620,878, issued Nov. 4, 1986, relating to microemulsions, each of which is incorporated herein by reference.

When the composition is intended for aerosol application, propellant gases can be included such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether. Where the solvent system is alcohol free, mechanical and chemical drying agents may also be employed in spray and aeroxol formulations.

It will be apparent from the foregoing that many other variations and modifications may be made in the compounds, compositions, and methods, described herein, without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. In a hair treating method for imparting curl retention to hair in which at least one film forming ingredient is applied to the hair as a mixture including the film forming ingredient dissolved in a solvent, the improvement comprising utilizing as the film forming ingredient an organosilicon compound having a formula selected from the group consisting of

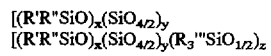

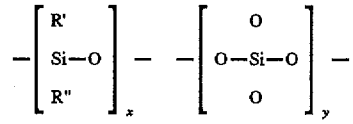

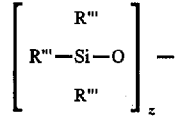

and hydroxy, alkoxy, aryloxy, and alkenoxy, derivatives thereof, wherein R, R', R", and R''', are selected from the group consisting of alkyl, alkenyl, aryl, and alkylaryl, radicals having from one to twenty carbon atoms; x and z are each integers having a value of from zero to about one thousand provided either x or z is at least 1; y is an integer having a value from about one to about one thousand; and the organosilicon compound is present in the mixture at a level from about 0.1 to about fifty percent by weight based on the weight of the mixture.

2. The method of claim 1 in which the organosilicon compound is present in the mixture at a level from about three to about thirty percent by weight based on the weight of the mixture.

3. The method of claim 1 in which the solvent is selected from the group consisting of water, volatile cyclic silicones, aliphatic hydrocarbons, aliphatic alcohols, mixtures of alcohol and water, and organic ethers.

4. The method of claim 3 in which the hydrocarbon is selected from the group consisting of liquefied petroleum gas, propane and isobutane.

5. The method of claim 3 in which the alcohol is selected from the group consisting of ethanol and isopropanol.

6. The method of claim 1 in which the organosilicon compound is applied to the hair as a mixture including the solvent and at least one additional ingredient selected from the group consisting of propellants, conditioners, surfactants, plasticizers, thickenerst, preservatives, and fragrances.

7. The method of claim 1 in which the solvent is supercritical carbon dioxide.

8. The method of claim 1 in which the solvent is supercritical nitrogen.

9. The method of claim 3 in which the ether is dimethylether.

* * * * *